United States Patent
Elibol et al.

(10) Patent No.: US 9,551,682 B2
(45) Date of Patent: Jan. 24, 2017

(54) HIGH THROUGHPUT BIOCHEMICAL DETECTION USING SINGLE MOLECULE FINGERPRINTING ARRAYS

(75) Inventors: Oguz H. Elibol, Plao Alto, CA (US); Grace M. Credo, San Mateo, CA (US); Xing Su, Cupertino, CA (US); Madoo Varma, Palo Alto, CA (US); Jonathan S. Daniels, Palo Alto, CA (US); Drew Hall, Santa Clara, CA (US); Handong Li, Santa Clara, CA (US); Noureddine Tayebi, Palo Alto, CA (US); Kai Wu, Mountain View, CA (US)

(73) Assignee: INTEL CORPORATION, Santa Clara, CA (US)

( * ) Notice: Subject to any disclaimer, the term of this patent is extended or adjusted under 35 U.S.C. 154(b) by 1140 days.

(21) Appl. No.: 13/538,346

(22) Filed: Jun. 29, 2012

(65) Prior Publication Data

US 2014/0001055 A1    Jan. 2, 2014

(51) Int. Cl.
| | | |
|---|---|---|
| *G01N 27/327* | (2006.01) | |
| *B82Y 15/00* | (2011.01) | |
| *C40B 20/04* | (2006.01) | |
| *C40B 50/16* | (2006.01) | |

(52) U.S. Cl.
CPC .......... *G01N 27/3278* (2013.01); *B82Y 15/00* (2013.01); *B01J 2219/00608* (2013.01); *B01J 2219/00653* (2013.01); *B01J 2219/00722* (2013.01); *C40B 20/04* (2013.01); *C40B 50/16* (2013.01); *G01N 27/3277* (2013.01)

(58) Field of Classification Search
CPC ....... B82Y 15/00; B82Y 5/00; G01N 27/3278; G01N 27/3277; B01J 2219/00722; B01J 2219/00725; B01J 2219/00727; B01J 2219/00729; C40B 20/04; C40B 20/00
See application file for complete search history.

(56) References Cited

U.S. PATENT DOCUMENTS

| | | |
|---|---|---|
| 2007/0292855 A1 | 12/2007 | Dubin et al. |
| 2009/0170716 A1* | 7/2009 | Su et al. ............ 506/9 |
| 2011/0037486 A1 | 2/2011 | Zhang et al. |

* cited by examiner

*Primary Examiner* — Matthew Martin
*Assistant Examiner* — Maris R Kessel
(74) *Attorney, Agent, or Firm* — Pillsbury Winthrop Shaw Pittman LLP

(57) ABSTRACT

Various embodiments provide devices, methods, and systems for high throughput biomolecule detection using transducer arrays. In one embodiment, a transducer array made up of transducer elements may be used to detect byproducts from chemical reactions that involve redox genic tags. Each transducer element may include at least a reaction chamber and a fingerprinting region, configured to flow a fluid from the reaction chamber through the fingerprinting region. The reaction chamber can include a molecule attachment region and the fingerprinting region can include at least one set of electrodes separated by a nanogap for conducting redox cycling reactions. In embodiments, by flowing the chamber content obtained from a reaction of a latent redox tagged probe molecule, a catalyst, and a target molecule in the reaction chamber through the fingerprinting region, the redox cycling reactions can be detected to identify redox-tagged biomolecules.

27 Claims, 12 Drawing Sheets

HIGH THROUGHPUT BIOCHEMICAL DETECTION USING SINGLE MOLECULE FINGERPRINTING ARRAYS

CROSS-REFERENCE TO RELATED APPLICATIONS

Reference is made to commonly owned and co-pending U.S. application Ser. No. 12/655,578 entitled "Nanogap Chemical and Biochemical Sensors," filed Dec. 31, 2009, now pending; U.S. patent application Ser. No. 11/226,696, entitled "Sensor Arrays and Nucleic Acid Sequencing Applications," filed Sep. 13, 2005, now pending; which is a continuation-in-part application that claims the benefit of U.S. patent application Ser. No. 11/073,160, entitled "Sensor Arrays and Nucleic Acid Sequencing Applications," filed Mar. 4, 2005; U.S. patent application Ser. No. 11/967,600, entitled "Electronic Sensing for Nucleic Acid Sequencing," filed Dec. 31, 2007 now pending; U.S. patent application Ser. No. 12/319,168, entitled "Nucleic Acid Sequencing and Electronic Detection," filed Dec. 31, 2008, now pending; U.S. patent application Ser. No. 12/459,309, entitled "Chemically Induced Optical Signals and DNA Sequencing," filed Jun. 30, 2009, now pending; U.S. patent application Ser. No. 12/655,459, entitled "Solid-Phase Chelators and Electronic Biosensors," filed Dec. 30, 2009, now pending; U.S. patent application Ser. No. 12/823,995, entitled "Nucleotides and Oligonucleotides for Nucleic Acid Sequencing," filed Jun. 25, 2010, now pending; U.S. patent application Ser. No. 12/860,462, entitled "Nucleic Acid Sequencing," filed Aug. 20, 2010, now pending; International Patent Application PCT/US2011/067520, entitled "Nanogap Transducers with Selective Surface Immobilization Sites," filed Dec. 28, 2011; and International Patent Application PCT/US2011/065154, entitled "Diamond Electrode Nanogap Transducers," filed Dec. 15, 2011; the disclosures of which are incorporated herein by reference. Appropriate components for device/system/method/process aspects of the each of the foregoing patents and patent publications may be selected for the present disclosure in embodiments thereof.

FIELD OF THE INVENTION

This disclosure relates generally to devices, methods, and systems for high throughput biochemical detection using sensor arrays, and more particularly, to devices, methods, and systems using arrays of electronic transducer elements for single molecule fingerprinting coupled with electronic readout systems.

BACKGROUND INFORMATION

Conventional methods for biomolecule detection such as DNA sequencing include use of optical detection technologies. Among existing optical methods, an array of wells is used to immobilize polymerase molecules and to act as zero mode waveguides such that only the fluorescence near the surface and at the polymerase is detected. Although incorporation of a modified nucleotide is observed via fluorescent tags, problems arise. The problems are associated with the capture and fluorescence efficiency of the single molecule signal. Namely the laser used in the fluorophore excitation heats the enzymes, reducing the read length in each well and ultimately compromising the accuracy of the system. In addition, enzymes immobilized in the wells become inactive and the sequences in these wells cannot be read.

In general, important parameters for evaluating a sequencing technique include accuracy, cost, throughput, time to result, and system size. For example, the tolerable level of error is accepted to be 1 in 10,000 bases sequenced. With this level of accuracy, existing systems are bulky with high cost and take long time to sequence a human genome. For example, large optical detection systems are used for human genome sequencing (3 billion base pairs) with sizes comparable to a refrigerator and the cost is about $30K in reagents (excluding the overhead cost of the sequencer) with about a week or longer to complete. In another example for CMOS-based sequencing methods, over 1000 chips were used with a reported cost exceeding $2 million to extract the full genome of Gordon Moore.

There is a need for providing devices, methods, and systems for portable, accurate, cost effective, easy-to-use, and high throughput biochemical detections.

BRIEF DESCRIPTION OF THE DRAWINGS

In the drawings, like reference numerals refer to like parts throughout the various views of the non-limiting and non-exhaustive embodiments of the present invention, and wherein.

DETAILED DESCRIPTION OF THE INVENTION

Figure 1:
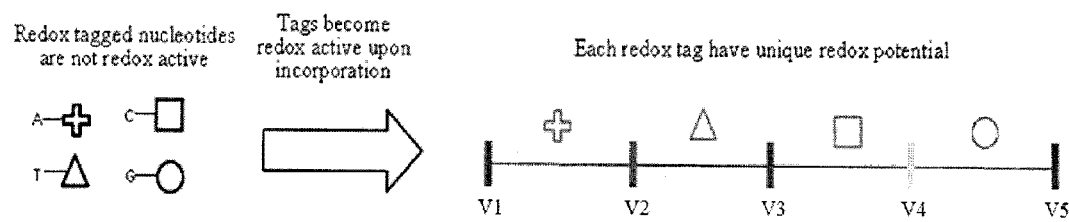
FIG. 1 is a scheme showing four redox-tagged nucleotides in accordance with various embodiments of the present teachings.

As used in the specification and claims, the singular forms "a", "an" and "the" include plural references unless the context clearly dictates otherwise. For example, the term "an array" may include a plurality of arrays unless the context clearly dictates otherwise.

Reference throughout this specification to "one embodiment" or "an embodiment" means that a particular feature, structure, or characteristic described in, connection with the embodiment is included in at least one embodiment of the present invention. Thus, the appearance of the phrases "in one embodiment" or "in an embodiment" in various places throughout this specification are not necessarily all referring to the same embodiment. Furthermore, the particular features, structures, or characteristics may be combined in any suitable manner in one or more embodiments.

Embodiments provide devices, methods, and systems for high throughput biomolecule sensing, detecting, and/or sequencing using sensor arrays, for example, arrays of electronic transducer elements for single molecule fingerprinting coupled with electronic readout systems. In embodiments, the biomolecules, e.g., a nucleotide, a polynucleotide, an oligonucleotide, a peptide, a protein, a ligand, a receptor, etc., that need to be sensed, detected, and/or determined can be redox-tagged for sensing, detecting, sequencing, and/or determination. In the following description, numerous specific details are provided, as the identification of various system components, to provide a thorough understanding of embodiments of the invention. One skilled in the art will recognize, however, that embodiments of the invention can be practiced without one or more of the specific details, or with other methods, components, materials, etc. In still other instances, well known structures, materials, or operations are not shown or described in detail to avoid obscuring aspects of various embodiments of the invention.

An "array" "macroarray" or "microarray" is an intentionally created collection of substances, such as molecules, microcoils, detectors, transducers and/or sensors, attached to, as a part of, or fabricated on a substrate or solid surface, such as glass, plastic, silicon chip or other material forming an array.

A "transducer array" is an array of transducers or transducer elements each including a transducer along with other related components. A transducer converts one form of energy, or signal, to another. Energy types include (but are not limited to) electrical, mechanical, electromagnetic (including light), chemical, acoustic or thermal energy. While the term transducer commonly implies the use of a sensor/detector, any device which converts energy can be considered a transducer.

A "transducer element" includes components incorporated with a transducer that converts one form of energy, or signal, to another, and vice versa. For example, a transducer element could include at least a reaction chamber and a fingerprinting region including a transducer capable of converting chemical energy to electrical energy, and vice versa, and configured such that a fluid in the reaction chamber is capable of flowing through the fingerprinting region.

"Substrate" "support" and "solid support" refer to a material or group of materials having a rigid or semi-rigid surface or surfaces.

The term "analyte" "target" or "target molecule" refers to a molecule of interest that is to be detected and/or analyzed, e.g., a nucleotide, an oligonucleotide, a polynucleotide, a peptide, or a protein. The analyte, target or target molecule could be a small molecule, biomolecule, or nanomaterial such as but not necessarily limited to a small molecule that is biologically active, nucleic acids and their sequences, peptides and polypeptides, as well as nanostructure materials chemically modified with biomolecules or small molecules capable of binding to molecular probes such as chemically modified carbon nanotubes, carbon nanotube bundles, nanowires, nanoclusters or nanoparticles.

The term "capture molecule" refers to a molecule that is immobilized on a surface. The capture molecule generally, but not necessarily, binds to a target or target molecule. The capture molecule is typically an antibody, a nucleotide, an oligonucleotide, a polynucleotide, a peptide, or a protein, but could also be a small molecule, biomolecule, or nanomaterial such as but not necessarily limited to a small molecule that is biologically active, nucleic acids and their sequences, peptides and polypeptides, as well as nanostructure materials chemically modified with biomolecules or small molecules capable of binding to a target molecule that is bound to a probe molecule to form a complex of the capture molecule, target molecule and the probe molecule. In the case of a solid-phase immunoassay, the capture molecule in immobilized on the surface of the substrate and is an antibody specific to the target, an antigen, to be detected. The capture molecule may be fluorescently labeled antibody, protein, DNA or RNA. The capture molecule may or may not be capable of binding to just the target molecule or just the probe molecule.

The term "probe" or "probe molecule" refers to a molecule that binds to a target molecule for the analysis of the target. The probe or probe molecule is generally, but not necessarily, has a known molecular structure or sequence.

A "binding partner," refers to a molecule or aggregate that has binding affinity for one or more analytes, targets or other molecules. In this sense, a binding partner is either a "capture molecule" or a "probe molecule." Within the scope of the embodiments of the invention, virtually any molecule or aggregate that has a binding affinity for an analyte or target of interest may be a binding partner, including, but are not limited to, polyclonal antibodies, monoclonal antibodies, single-chain antibodies, chimeric antibodies, humanized antibodies, antibody fragments, oligonucleotides, polynucleotides, nucleic acids, aptamers, nucleic acid ligands and any other known ligand that can bind to at least one target molecule. Although, in certain embodiments a binding partner is specific for binding to a single target, in other embodiments the binding partner may bind to multiple targets that possess similar structures or binding domains.

"Binding" refers to an interaction between two or more substances, such as between a target and a capture or probe molecule, that results in a sufficiently stable complex so as to permit detection of the bound molecule complex. In certain embodiments of the invention, binding may also refer to an interaction between a second molecule and a target.

"Associated with" or "association" refers to a direct or indirect interactions between two or more substances, such as between a target and a capture or probe molecule, that results in a sufficiently stable complex. For example, a molecule or complex of molecules is "associated with" the surface of a substrate when the molecule or complex is either bound to the surface of the substrate directly, through another molecule or substance, or to both. In other words, substances are "associated with" each other when any one member of the substances is directly bound to at least another member of the substances. Additionally, a component of an integrated device is also "associated with" the device. For example, a transistor in an integrated circuit is "associated with" the circuit.

The terms "label," "tag" and "sensor compound" are used interchangeably to refer to a marker or indicator distinguishable by the observer but not necessarily by the system used to identify an analyte or target. A label may also achieve its effect by undergoing a pre-designed detectable process. Labels are often used in biological assays to be conjugated with, or attached to, an otherwise difficult to detect substance. At the same time, Labels usually do not change or affect the underlining assay process. A label or tag used in biological assays include, but not limited to, a redox-active molecule.

The term "chip" or "microchip" refers to a microelectronic device made of semiconductor material and having one or more integrated circuits or one or more devices. A "chip" or "microchip" is typically a section of a wafer and made by slicing the wafer. A "chip" or "microchip" may comprise many miniature transistors and other electronic components on silicon, sapphire, germanium, silicon nitride, silicon germanium, or of any other semiconductor material. A microchip can contain dozens, hundreds, or millions of electronic components. A chip could be a biochip, for example.

The term "processor" may refer to any device or portion of a device that processes electronic data from registers and/or memory to transform that electronic data into other electronic data that may be stored in registers and/or memory.

The term "biomolecule" refers to any organic molecule that is part of a living organism. Biomolecules includes a nucleotide, a polynucleotide, an oligonucleotide, a peptide, a protein, a ligand, a receptor, among others. A "complex of a biomolecule" refers to a structure made up of two or more types of biomolecules. Examples of a complex of biomolecule include a cell or viral particles. A cell can include bacteria, fungi, animal mammalian cell, for example.

The term "nucleotide" includes deoxynucleotides and analogs thereof. These analogs are those molecules having some structural features in common with a naturally occurring nucleotide such that when incorporated into a polynucleotide sequence, they allow hybridization with a complementary polynucleotide in solution. Typically, these analogs are derived from naturally occurring nucleotides by replacing and/or modifying the base, the ribose or the phosphodiester moiety. The changes can be tailor-made to stabilize or destabilize hybrid formation, or to enhance the specificity of hybridization with a complementary polynucleotide sequence as desired, or to enhance stability of the polynucleotide.

The term "polynucleotide" or "polynucleic acid" as used herein refers to a polymeric form of nucleotides of any length, either ribonucleotides or deoxyribonucleotides, that comprise purine and pyrimidine bases, or other natural, chemically or biochemically modified, non-natural, or derivatized nucleotide bases. Polynucleotides of the embodiments of the invention include sequences of deoxyribopolynucleotide (DNA), ribopolynucleotide (RNA), or DNA copies of ribopolynucleotide (cDNA) which may be isolated from natural sources, recombinantly produced, or artificially synthesized. A further example of a polynucleotide of the embodiments of the invention may be polyamide polynucleotide (PNA). The polynucleotides and nucleic acids may exist as single-stranded or double-stranded. The backbone of the polynucleotide can comprise sugars and phosphate groups, as may typically be found in RNA or DNA, or modified or substituted sugar or phosphate groups. A polynucleotide may comprise modified nucleotides, such as methylated nucleotides and nucleotide analogs. The sequence of nucleotides may be interrupted by non-nucleotide components. The polymers made of nucleotides such as nucleic acids, polynucleotides and polynucleotides may also be referred to herein as "nucleotide polymers.

An "oligonucleotide" is a polynucleotide having 2 to 20 nucleotides. Analogs also include protected and/or modified monomers as are conventionally used in polynucleotide synthesis. As one of skill in the art is well aware, polynucleotide synthesis uses a variety of base-protected nucleoside derivatives in which one or more of the nitrogen atoms of the purine and pyrimidine moiety are protected by groups such as dimethoxytrityl, benzyl, tert-butyl, isobutyl and the like.

For instance, structural groups are optionally added to the ribose or base of a nucleoside for incorporation into a polynucleotide, such as a methyl, propyl or allyl group at the 2'-O position on the ribose, or a fluoro group which substitutes for the 2'-O group, or a bromo group on the ribonucleoside base. 2'-O-methyloligoribonucleotides (2'-O-MeORNs) have a higher affinity for complementary polynucleotides (especially RNA) than their unmodified counterparts. Alternatively, deazapurines and deazapyrimidines in which one or more N atoms of the purine or pyrimidine heterocyclic ring are replaced by C atoms can also be used.

The phosphodiester linkage or "sugar-phosphate backbone" of the polynucleotide can also be substituted or modified, for instance with methyl phosphonates, O-methyl phosphates or phosphororthioates. Another example of a polynucleotide comprising such modified linkages for purposes of this disclosure includes "peptide polynucleotides" in which a polyamide backbone is attached to polynucleotide bases, or modified polynucleotide bases. Peptide polynucleotides which comprise a polyamide backbone and the bases found in naturally occurring nucleotides are commercially available.

Nucleotides with modified bases can also be used in the embodiments of the invention. Some examples of base modifications include 2-aminoadenine, 5-methylcytosine, 5-(propyn-1-yl)cytosine, 5-(propyn-1-yl)uracil, 5-bromouracil, 5-bromocytosine, hydroxymethylcytosine, methyluracil, hydroxymethyluracil, and dihydroxypentyluracil which can be incorporated into polynucleotides in order to modify binding affinity for complementary polynucleotides.

Groups can also be linked to various positions on the nucleoside sugar ring or on the purine or pyrimidine rings which may stabilize the duplex by electrostatic interactions with the negatively charged phosphate backbone, or through interactions in the major and minor groves. For example, adenosine and guanosine nucleotides can be substituted at the N2 position with an imidazolyl propyl group, increasing duplex stability. Universal base analogues such as 3-nitropyrrole and 5-nitroindole can also be included. A variety of modified polynucleotides suitable for use in the embodiments of the invention are described in the literature.

When the macromolecule of interest is a peptide, the amino acids can be any amino acids, including α, β, or ω-amino acids. When the amino acids are α-amino acids, either the L-optical isomer or the D-optical isomer may be used. Additionally, unnatural amino acids, for example, β-alanine, phenylglycine and homoarginine are also contemplated by the embodiments of the invention. These amino acids are well-known in the art.

A "peptide" is a polymer in which the monomers are amino acids and which are joined together through amide bonds and alternatively referred to as a polypeptide. In the context of this specification it should be appreciated that the amino acids may be the L-optical isomer or the D-optical isomer. Peptides are two or more amino acid monomers long, and often more than 20 amino acid monomers long.

A "protein" is a long polymer of amino acids linked via peptide bonds and which may be composed of two or more polypeptide chains. More specifically, the term "protein" refers to a molecule composed of one or more chains of amino acids in a specific order; for example, the order as determined by the base sequence of nucleotides in the gene coding for the protein. Proteins are essential for the structure, function, and regulation of the body's cells, tissues, and organs, and each protein has unique functions. Examples are hormones, enzymes, and antibodies.

The term "sequence" refers to the particular ordering of monomers within a macromolecule and it may be referred to herein as the sequence of the macromolecule.

The term "hybridization" refers to the process in which two single-stranded polynucleotides bind non-covalently to form a stable double-stranded polynucleotide; triple-stranded hybridization is also theoretically possible. The resulting (usually) double-stranded polynucleotide is a "hybrid." The proportion of the population of polynucleotides that forms stable hybrids is referred to herein as the "degree of hybridization." For example, hybridization refers to the formation of hybrids between a probe polynucleotide (e.g., a polynucleotide of the invention which may include substitutions, deletion, and/or additions) and a specific target polynucleotide (e.g., an analyte polynucleotide) wherein the probe preferentially hybridizes to the specific target polynucleotide and substantially does not hybridize to polynucleotides consisting of sequences which are not substantially complementary to the target polynucleotide. However, it will be recognized by those of skill that the minimum length of a polynucleotide desired for specific hybridization to a target polynucleotide will depend on several factors: G/C content, positioning of mismatched bases (if any), degree of uniqueness of the sequence as compared to the population of target polynucleotides, and chemical nature of the polynucleotide (e.g., methylphosphonate backbone, phosphorothiolate, etc.), among others.

Methods for conducting polynucleotide hybridization assays have been well developed in the art. Hybridization assay procedures and conditions will vary depending on the application and are selected in accordance with the general binding methods known in the art.

It is appreciated that the ability of two single stranded polynucleotides to hybridize will depend upon factors such as their degree of complementarity as well as the stringency of the hybridization reaction conditions.

A "ligand" is a molecule or a portion of a molecule that is recognized by a particular receptor. Examples of ligands that can be investigated by this invention include, but are not restricted to, agonists and antagonists for cell membrane receptors, toxins and venoms, viral epitopes, hormones, hormone receptors, peptides, enzymes, enzyme substrates, cofactors, drugs (e.g. opiates, steroids, etc.), lectins, sugars, polynucleotides, nucleic acids, oligosaccharides, proteins, and monoclonal antibodies.

A "receptor" is molecule that has an affinity for a given ligand. Receptors may-be naturally-occurring or manmade molecules. Also, they can be employed in their unaltered state or as aggregates with other species. Receptors may be attached, covalently or noncovalently, to a binding member, either directly or via a specific binding substance. Examples of receptors which can be employed by this invention include, but are not restricted to, antibodies, cell membrane receptors, monoclonal antibodies and antisera reactive with specific antigenic determinants (such as on viruses, cells or other materials), drugs, polynucleotides, nucleic acids, peptides, cofactors, lectins, sugars, polysaccharides, cells, cellular membranes, and organelles. Receptors are sometimes referred to in the art as anti-ligands. As the term "receptors" is used herein, no difference in meaning is intended. A "Ligand Receptor Pair" is formed when two macromolecules have combined through molecular recognition to form a complex.

The term "complementary" refers to the topological compatibility or matching together of interacting surfaces of a ligand molecule and its receptor. Thus, the receptor and its ligand can be described as complementary, and furthermore, the contact surface characteristics are complementary to each other.

A chip, microchip, IC chip, or IC device can be various sizes and shapes. It can be used as a substrate for a microchip. The circuitry in the chip can also serve several purposes, for example, as microprocessors, memory storage, and/or communication capabilities.

Embodiments provide devices, methods, and systems for high throughput biomolecule sensing and detection using sensor arrays, for example, arrays of electronic transducer elements for single molecule fingerprinting, coupled with electronic readout systems. By using the disclosed devices, methods, and systems, for example, the human genome may be sequenced in less than a day using a desktop system (or smaller) that utilizes a silicon chip on order of $cm^2$ in area.

In embodiments, a device used for sensing, detecting and/or sequencing biomolecules such as DNAs, proteins, and/or other biomolecules as disclosed herein, may include a transducer array that is made up of a plurality of transducer elements. In embodiments, a large array of the transducer elements can be used, for example, to sequence a complex genome. The array may contain thousands to millions or billions of transducer elements. For example, the transducer array may include about 2 to about 10,000,000,000, or about 2 to about 10,000,000*, such as about 2 to about 1,000,000, transducer elements. The transducer element may have a linear dimension of, e.g., about 0.1 to 100 micrometers, or any dimensions, occupying up to about 10000 micron squared area. In one example, a transducer element may occupy 100 micron squared area (e.g., 5 microns×20 microns) and capable of sequencing an effective 1 kilo bases or more, such as about 10 kilo bases or more. In this case, 1 billion DNA bases can be sequenced in a 1 $cm^2$ area of silicon, making the technology significantly attractive especially for whole human genome sequencing.

The transducer element may include an inlet region, a fingerprinting region, and an outlet region configured such that a fluid in the inlet region is capable of flowing through the fingerprinting region to the outlet region.

The inlet region of each transducer element may include a reaction chamber having a molecule attachment region. The molecule attachment region can have a surface capable of attaching one or more molecules thereto. In embodiments, the molecule attachment region may have a single or multiple biomolecules attached thereto, and/or provide surfaces capable of attaching a single molecule or a plurality of molecules to be analyzed. When the molecule attachment region contains a single molecule to be analyzed or a single attachment site for a molecule to be analyzed, the molecule attachment region is referred to as a single molecule attachment region. For example, the molecule attachment region can have different levels of modification. In embodiments, the molecule attachment region can include one or more of the following, enzymes, peptides, and/or nucleic acids. Depending on stability and robustness requirements of device applications, such molecules of enzymes, peptides, and/or nucleic acids can be fully or partially "built-in".

Alternatively, enzymes, peptides, and/or nucleic acids can be stored separately and immobilized onto the molecule attachment region of the device. The molecule attachment region can comprise molecules capable of attaching enzymes, peptides, and/or nucleic acids. In some embodiments, the molecule attachment region can include already-immobilized probes capable of hybridizing to a nucleic acid to be analyzed, such as, for example polynucleotide probes or DNA probes. In other embodiments, the molecule attachment region can include a $SiO_2$ area functionalized with a silane mixture that allows for the attachment of a probe and or single molecule of DNA by the end user. In embodiments, peptides in array can be attached to the single molecule attachment region for further cell adhesion, enzyme activity and/or protein binding assays. The attached peptides can also be a "built-in" part of the fingerprinting detection device.

The reaction chamber may contain chamber content such as a fluid including, for example, reactants for undergoing reactions in the reaction chamber, reaction product, reaction by-products, and/or any fluid. As desired, the reaction content including for example the reaction by-products may be forced to flow from the reaction chamber to pass through the fingerprinting region and/or into an outlet region.

The fingerprinting region of each transducer element may include at least one electrode set having a first electrode and a second electrode separated by a gap there-between. The gap can be a nanometer sized gap (i.e., nanogap) of less than about 500 nm, e.g., for conducting redox cycling reactions. In embodiments, the transducer element may also be referred to as nanogap transducer. The nanogap between electrodes can be between 10 and 500 nm, for example, between 10 and 200 nm, such as about 50 nm for conducting redox cycling. In embodiments, the fingerprinting region of each transducer element may include at least one electrode set. For example, the fingerprinting region of each transducer element may include four electrode sets or more. Each electrode set may include a pair of electrodes separated by a nanogap for conducting redox cycling. In an embodiment, the electrodes are each capable of being independently biased, monitored, and detected.

In general, redox cycling is an electrochemical method in which a molecule that can be reversibly oxidized and/or reduced (i.e., a redox active molecule) moves between at least two electrodes that are biased independently, one below a reduction potential and the other one above an oxidation potential for the redox active molecule being detected, shuttling electrons between the independently biased electrodes (i.e., the molecule is oxidized at a first electrode and then diffuses to a second electrode where it is reduced or vice versa, it is first reduced and then oxidized, depending on the molecule and the potentials at which the electrodes are biased). The same molecule can therefore contribute a plurality of electrons to the recorded current resulting in the net amplification of the signal. In a redox cycling measurement, oppositely biased electrodes are used to repeatedly flip the charge state of redox active molecules in solution allowing each redox active molecule to participate in multiple redox reactions and thereby contribute multiple electrons to a measured current value. In redox cycling measurements, the height of the gap between the electrodes can be on the nanometer scale. Redox active molecules flow between the two electrodes shuttle multiple electrons between the electrodes, leading to amplification of the measured electrochemical current. Signals from the redox active species can potentially be amplified greater than 100 times, depending on factors such as the stability of the redox species and the ability of the redox species to diffuse out of the sensing region. In embodiments, electrodes in the nanogap are independently biased at the oxidation and reduction potential of the redox species to be detected. Redox species act as charge shuttles and the diffusion of the molecules from one electrode to the other results in the reduction and oxidation of the redox molecule and a net charge transfer. The magnitude of current through either electrode is proportional to the analyte (redox species) concentration in the cavity. In general, a redox active species is a molecule that is capable of reversibly cycling through states of oxidation and/or reduction a plurality of times.

To detect the signals from the redox cycling, the fingerprinting region having a nanogap is integrated with a reaction chamber where biomolecules, for example, proteins, peptides, RNAs, and/or DNAs such as a single DNA molecule and a single DNA polymerase are present. Because the nanogap can amplify a redox signal, a single redox species can be detected. The fingerprinting is therefore also referred to single molecule fingerprinting. Due to the signal amplification and multiplex detection, various types of redox signals can be detected in real-time, in situ. Single molecules can be sequenced without cyclic or sequential reagent changes required to synchronize reactions in each element of an array.

A readout circuitry can be coupled with the transducer array to read and interpret signals from each redox cycling of one or more transducer elements of the plurality of transducer elements in the transducer array. In embodiments, the transducer array may be disposed on e.g., an IC chip, formed on a substrate. The substrate may be a silicon substrate. The first electrode and the second electrode of the nanogap in each transducer element may be independently, electrically coupled to and/or individually (or in groups) addressable through electronics within the integrated circuit chip.

In general, electronic transducers or sensors employing electrodes are capable of measuring the impedance, the resistance, the capacitance, and/or the redox potential of the materials that are located on or near the electrode surface. The substrate on which the nanogap transducers reside may also include detection and/or drive circuits, logic for switching, latches, memory, and/or input/output devices. Optionally some or all of the electronics for sensing and driving electrodes and recording data are integrated circuits that are part of the substrate that houses an array of transducer elements. Electronics providing input and output control are optionally housed in the substrate, such as in an integrated circuit chip, or are provided through circuitry that is external the substrate. An array of transducer elements is optionally equipped with circuitry for individually (or in groups) addressing the electrodes, driving the electrodes at selected voltages, memory for storing voltage current information to be supplied to the electrodes, memory and microprocessors for measuring electrode characteristics, differential amplifiers, current-sensing circuits (including variants of circuits used in CMOS image sensors), and/or field effect transistors (direct and floating gate). Alternatively, one or more of these functions can be performed by external instruments and/or attached computer system(s).

An array of individually addressable nanogap transducers can be housed on and electrically coupled to an IC chip. The IC chip is typically built on a semiconductor substrate, such as, a semiconductor wafer that is diced apart to yield individual IC chips. The base substrate on which an IC chip is built is typically a silicon wafer, although embodiments of the invention are not dependent on the type of substrate used. The substrate can also be comprised of germanium, indium antimonide, lead telluride, indium arsenide, indium phosphide, gallium arsenide, gallium antimonide, and/or other group III-V materials either alone or in combination with silicon or silicon dioxide or other insulating materials. Layers and layers including devices can also be described as the substrate or part of the substrate on which embodiments of the invention are housed or fabricated.

In one embodiment, the plurality of transducer elements may be disposed on top of standard CMOS (complementary metal oxide semiconductor) circuits via monolithic integration. The transducer array may be formed in a post processed layer of the CMOS device layer. For example, transducers having nanogaps (or nanogap transducers) can be reliably fabricated in a CMOS compatible manner allowing dense integration of the DNA sequencing devices onto a single platform of a chip or silicon wafer. The transducer elements such as nanogap transducers may be provided very small. For example, an individual transducer can, for example, occupy as little as 0.5 $\mu m^2$ on an array or other chip surface. In other embodiments an individual transducer element may occupy from 0.5 $\mu m^2$ to 200 $\mu m^2$ or from 0.5 $\mu m^2$ to 100 $\mu m^2$ such as about 100 $\mu m^2$ of area arranged on an array or other chip surface.

Arrays of transducer elements may be built having a variety of dimensions and numbers of transducer elements such as nanogap transducers. The selection of number layout of transducer elements is informed by factors such as, for example, the types and numbers of analytes to be detected, the size of the fingerprinting regions, and costs involved in manufacturing the arrays. For example, arrays of nanogap transducers are 10×10, 100×100, 1,000×1,000, $10^5 \times 10^5$, and $10^6 \times 10^6$.

To drive a fluid to travel from the inlet region to the outlet region through the fingerprinting region of each transducer element, an active drift mechanism, such as, for example, a hydrodynamic mechanism, a heating element (e.g., a resistor heating element, a heater including a nanowire heater, etc.), and/or a sealing component may be incorporated with the transducer elements. The active drift mechanism may be configured to simultaneously or sequentially flow the fluid from one or more inlet regions of the transducer array. The active drift mechanism may be configured to simultaneously or sequentially flow the fluid (e.g., chamber content, reaction reagents, reaction byproducts, reaction product, etc.) from one or more inlet regions of the transducer array through the nanogaps of the fingerprinting regions and/or to the outlet regions. Accordingly, DNA sequencing processes can be performed simultaneously or sequentially in selected or all transducer elements of the transducer array.

The disclosed device for DNA sequencing may further include supporting fluidic subsystems. For example, a first fluidic system may be aligned on the inlet regions of the transducer array to supply the fluid in the reaction chambers of the inlet regions and to maintain a unidirectional flow through each fingerprinting region. In addition, a second fluidic system may be aligned on the outlet regions of the transducer array to maintain the unidirectional flow from each fingerprinting region in the transducer array.

In embodiments, some or all of the parts of a system for driving electrodes of the transducer array and measuring and recording current flow can be located in one integrated circuit (IC) chip that is electrically coupled to an array of individually addressable nanogap transducers housed on the IC chip. In embodiments, a computer system associated with the array of individually (or in groups) addressable nanogap transducers may include software for measuring and recording electrode potential and current values using measurements from only one electrode. In alternate embodiments the computer system may include software for measuring and recording electrode potentials from one or both of the two electrodes, if one electrode set is used. Techniques such as electrochemical correlation spectroscopy can be used to produce a signal from measurements from two oppositely biased electrodes in the nanogap transducer. Such sensing system therefore involves one or more of transducer arrays, supporting fluidic subsystems, readout systems, computer, data storage, related hardware, related software, and/or other possible functional parts.

A computer or computer system may be used including a processing system, including one or more processors that are communicatively coupled to one or more volatile or non-volatile data storage devices, such as random access memory (RAM), read-only memory (ROM), mass storage devices such as serial advanced technology attachment (SATA) or small computer system interface (SCSI) hard drives, and/or devices capable of accessing media, such as floppy disks, optical storage, tapes, flash memory, memory sticks, CD-ROMs and/or digital video disks (DVDs). The term ROM refers to non-volatile memory devices such as erasable programmable ROM (EPROM), electrically erasable programmable ROM (EEPROM), flash ROM, and/or flash memory. The processor can also be communicatively coupled to additional components, such as graphics controllers, memory interface hubs, SCSI (small computer system interface) controllers, network controllers, network interfaces, and universal serial bus (USB) controllers. Some or all of the communications between elements of the computer system, additional processors, and/or external computers and computer networks can also occur using various wired and/or wireless short range protocols including, USB, WLAN (wireless local area network), radio frequency (RF), satellite, microwave, Bluetooth, optical, fiber optical, infrared, cables, and lasers. Typically a computer system is also coupled to other input/output devices, such as, for example, display screens, keyboards, trackpads, mice.

The disclosed sensing devices/systems may be used to determine and assemble sequence information of a DNA fragment to be sequenced. For example, a single polymerase, a DNA fragment to be sequenced, and redox-tagged nucleotides may be provided in the reaction chamber of one or more transducer elements in the array. The single molecule polymerase enzyme may be immobilized on a surface of the reaction chamber, such as the molecule attachment region or the single molecule attachment region. The reaction chamber may also contain the DNA fragment to be sequenced. For example, the reaction chamber may contain one single polymerase molecule and the DNA fragment to be sequenced engaged with the polymerase. In further embodiments, a plurality of molecules, e.g., polymerase enzyme molecules, can be immobilized on surface of the reaction chamber. Redox-tagged nucleotides are redox-inactive before incorporation of the nucleotides and become redox-active after incorporation of the nucleotides by reversible reactions to release redox tags, e.g., from nucleoside-phosphate complexes. In embodiments, at least four redox-tagged nucleotides may be used with four redox tags respectively labeling four different nucleotides. Each redox tag has a specific redox electrical potential.

The redox-tagged nucleotides (or redox-tagged nucleotide analogs) may be used for real-time single molecule DNA sequencing. For example, the immobilized single molecule polymerase incorporates redox-tagged nucleotide in real-time in the reaction chamber and the resulting chamber content, e.g., including reaction by-products such as electronic redox tags with unique redox potentials, are then driven to flow through the fingerprinting region. Redox cycling between electrodes of the electrically biased electrode sets is then monitored and detected to identify corresponding redox-tagged nucleotides. In embodiments, integrated electronics may allow for very low current levels to be detected and processed. The order of the DNA bases in the DNA sequence attached to the transducer may be detected or read out by the order in which the unique redox tags are detected and/or then assembled. Each transducer element is able to read DNA fragments, for example, from 1 to 100 bases long, such as from 1 to 10 kilo bases long, although longer or shorter read lengths may also be read. The transducer array may contain on the order of a million transducer elements that can electrically fingerprint or identify single molecules released as chemical species. For whole genome sequencing a larger number of transducer elements can be incorporated in the array. Information from each transducer element is combined to yield the complete order and identity of every base in the genome under consideration.

FIG. 1 depicts four redox-tagged nucleotides (chemical building blocks of DNA) which are redox-inactive, but release redox tags (incorporation byproducts) having distinct redox potentials with reversible reactions being active only after incorporation. Each nucleotide is tagged with a unique molecule with distinct redox potentials. Redox cycling occurs at suitable potentials. In general, certain molecules can be oxidized by giving off electrons or reduced by accepting electrons. The potential at which a chemical species is oxidized or reduced is known as the redox potential. Each such redox-active chemical species has a characteristic redox potential which can be used to identify it. When a redox tag (which can go through a reversible redox reaction) is present in the nanogap and the electrodes are biased at suitable potentials, a redox tag can be oxidized and reduced. The signal is amplified through redox cycling by the rapid diffusion of the redox tag molecule between electrodes resulting in the signal amplification of the specific species. The shuttling frequency of the molecule (hence the current generated at a single electrode) is proportional to the diffusion coefficient and inversely proportional to the gap size. The current registered at the two electrodes due to the redox molecule shuttling is equal in magnitude and opposite in sign. This anticorrelated signal from electrodes can be further utilized to reduce or cancel out background current or noise from the detection electronics. Redox cycling allows for the current levels from a single tag molecule to be amplified and distinguished from other species in the transducer which may also have (a lower level of) redox behavior, as well as from random electronic noise in the interface circuitry.

As used herein, reversible redox molecules are used as the "tags" corresponding to DNA incorporation (and hence base sequence) which may then be detected electronically by the integrated circuitry. It is suitable to infer the signal from a single redox molecule with a nanogap transducer element. It is suitable to detect as many unique reactions as there are unique redox signals tags, because the characteristic redox potential of each tag molecule is different. In embodiments, by changing the electrical bias (or potential) in the time domain, single molecule fingerprinting can be performed on an arbitrary number of unique tags with only a single set of redox cycling electrodes.

Various embodiments also include detecting a number of specific redox reactions in parallel by having an array of transducer elements biased at appropriate potentials. For example, an electrical bias may be applied to at least one electrode set of each of one or more transducer elements of the plurality of transducer elements in the transducer array to monitor redox cycling in parallel in one or more transducer elements.

Conventional approaches to DNA sequencing includes "sequencing-by-synthesis" by detecting incorporation events of the complementary nucleotide to the priming strand, where the order of incorporation is determined by the sequence of the template DNA strand. Various readout means, e.g., by bioluminescence, fluorescence tags, pH change, etc were used. As disclosed herein, different than conventional approaches, a redox signal, in particular a single redox tag released per incorporation event (and only one priming strand per sensor site), is used for DNA sequencing. For example, when each of four nucleotides is tagged by a corresponding specific redox tag, e.g., through the terminal phosphate, a specific redox tag can be released when the corresponding nucleotide is incorporated to the priming strand according to the complementary base of the template strand. The incorporated base can be inferred by detecting the redox tag through the unique redox potential.

Figure 2A:
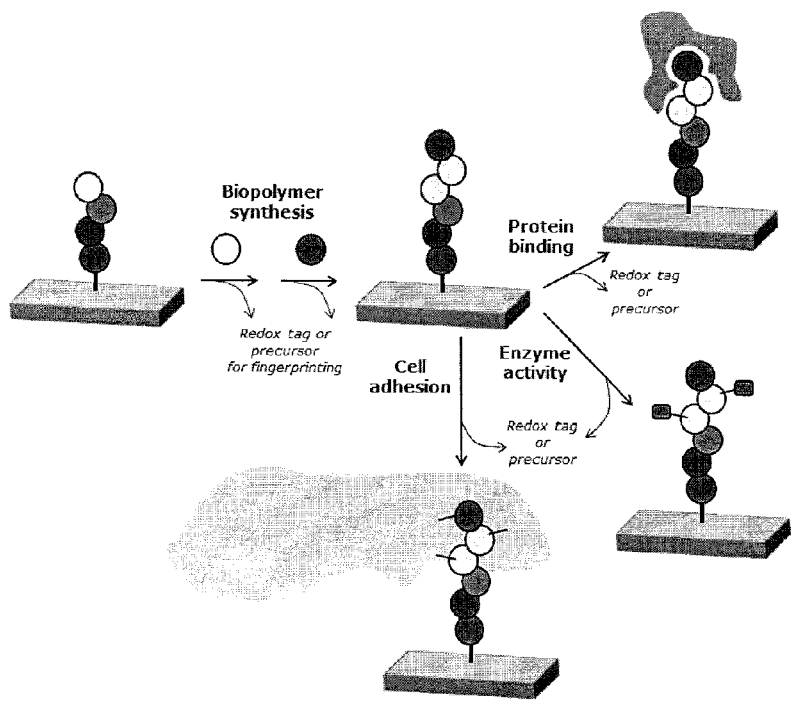
FIG. 2a depicts redox fingerprinting systems/methods for exemplary biomolecule detection applications in accordance with various embodiments of the present teachings.

FIG. 2a depicts redox fingerprinting systems/methods for exemplary biomolecule detection applications in accordance with various embodiments of the present teachings. The biomolecule detection applications may include, for example, biopolymer (e.g., DNA or peptide) synthesis, protein binding assays, enzyme activity assays, and cell adhesion assays as shown in FIG. 2a.

Figure 2B:
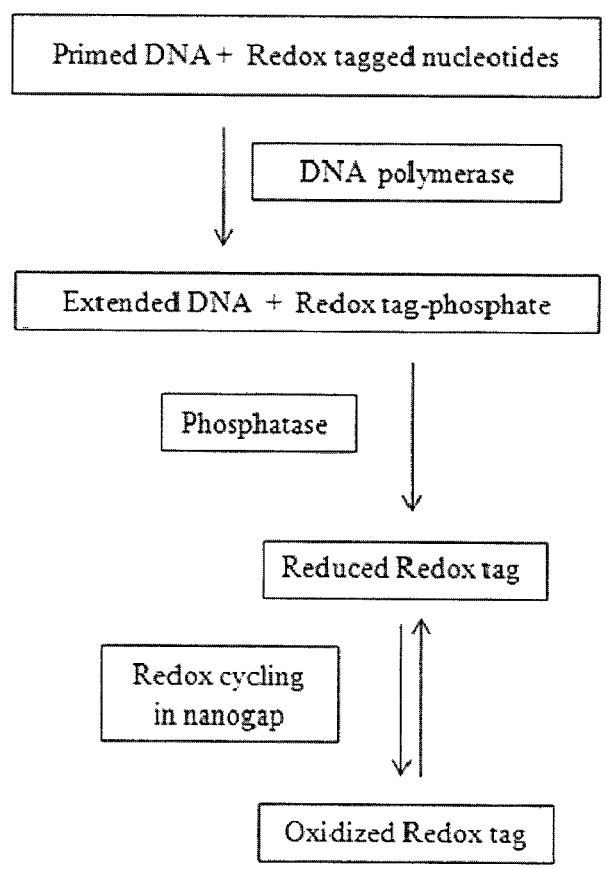
FIG. 2b is a flowchart of redox-genic species generation in DNA sequencing in accordance with various embodiments of the present teachings.
Figure 2C:
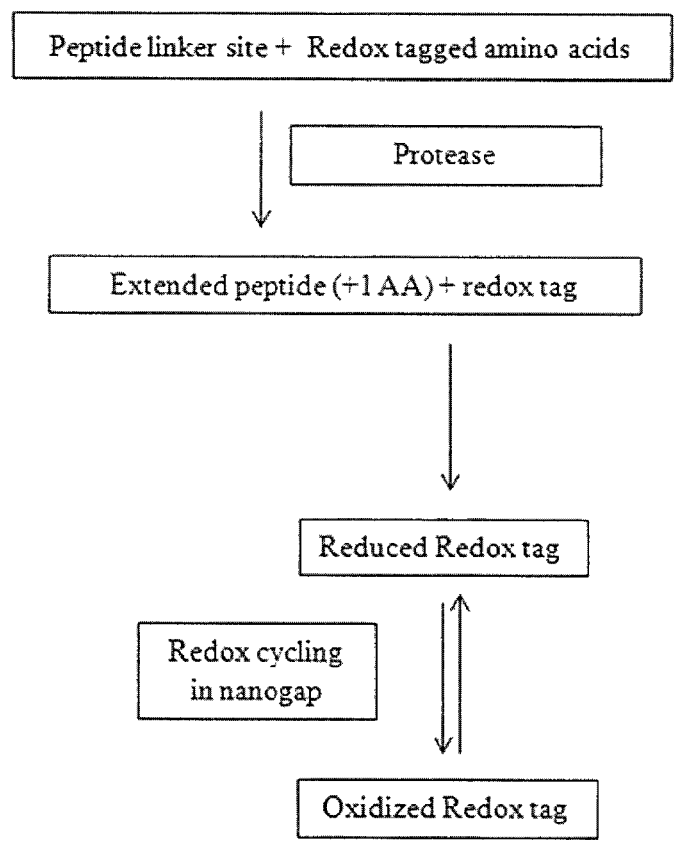
FIG. 2c is a flowchart of redox-genic species generation in peptide synthesis in accordance with various embodiments of the present teachings.
Figure 2D:
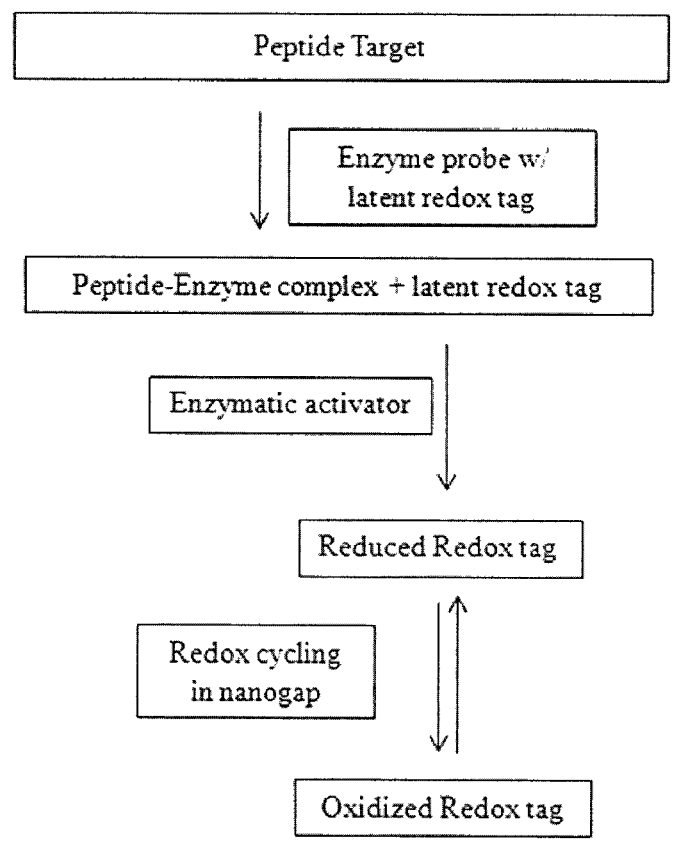
FIG. 2d is a flowchart of redox-genic species generation in a peptide activity assay in accordance with various embodiments of the present teachings.

FIGS. 2b-2d depict flowcharts of redox-genic species generation in DNA sequencing (see FIG. 2b), peptide synthesis (see FIG. 2c), and peptide activity assay (see FIG. 2d). For example, as shown in FIG. 2b, when a DNA polymerase, a primed DNA molecule to be sequenced, and redox-tagged nucleotides are placed in a reaction chamber, redox species, e.g., redox tag-phosphate, can be generated upon the incorporation of nucleotides. When the released redox species, e.g., by using phosphatase, enter the nanogap by drift, diffusion, or a combination of them, redox cycling reactions may take place between the electrodes of the nanogap in the fingerprinting region to generate an amplified signal that is a characteristic of the redox species and thus the corresponding incorporated nucleotide (base) is identified or fingerprinted.

In order to detect reaction products of a single base incorporation reaction, a single DNA polymerase and or a single DNA fragment to be analyzed can be confined to the reaction chamber. A specific material in a localized area in the reaction chamber may be compatible with specific surface chemistry. For example, a surface of the reaction chamber, such as the molecule attachment region, can be optionally functionalized with amine, aldehye, epoxy, thiol, groups, and molecules to be attached are functionalized with amine (for surface bearing carboxy, epoxy, and/or aldehyde functional groups) and carboxyl (for surface bearing amine groups), thiol (for surface of gold) to facilitate molecular attachment. Various conjugation chemistries are available to join the functional groups (for example, EDC for amine-carboxyl). The concentration of molecules on the substrate surface is controlled, for example, in several ways: by limiting the density of surface functional groups or by limiting the quantity of molecules to be attached. An enzyme and or a nucleic acid tethered in the reaction chamber can be attached to a surface in the chamber by a linking molecule. For anchoring the polymerase to a surface of the reaction chamber, unlike conventional optical approaches requiring the polymerase reaction and fluorescent reaction products to be within the evanescent field of an excitation laser, the polymerase proximity to a specific surface in a redox scheme is not a critical parameter, so the length of the linker and the movement of the polymerase can be optimized for other properties. In embodiments, the molecule attachment region can include, for example a small area of $SiO_2$ within a larger area of silicon oxynitride that covers the exposed regions of the reaction chamber, although other materials are also possible. A molecule attachment region that presents a small surface area allows the number of molecules attached in the reaction chamber to be controlled. For example, in embodiments, the molecule attachment region can have an exposed surface area of about 40 $nm^2$ to about 500,000 $nm^2$.

In various embodiments, biomolecules can be sensed, detected, and/or determined by detection of a byproduct from an enzymatic reaction by means of using redox genic tags. Redox genic means that the molecules are not capable of going through a redox reaction, i.e., redox inactive, unless through a specific enzymatic reaction. Such molecules may include latent redox tagged probe molecules. After going through the enzymatic reaction, the molecules become redox active allowing the inference of the enzymatic reaction. As disclosed herein, an "enzymatic reaction" encompasses any catalytic reactions.

For example, the disclosed fingerprinting detection may include a "positive test":

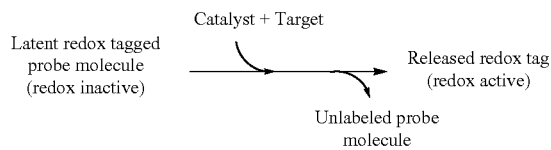

where latent redox tagged probe molecules that are redox inactive can be processed in the present of catalysts (or enzymes) and/or target molecules to produce unlabeled probe molecules and to release redox tags that are redox active.

In contrast, a "negative test" or control tests can be the following:

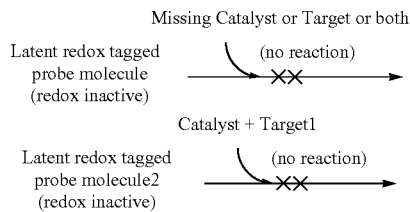

where none of the probe molecules and to release redox tags can be released, if any of the reaction components, e.g., catalysts and/or target molecules, are absent or non-reactive in the system.

Figure 3A:
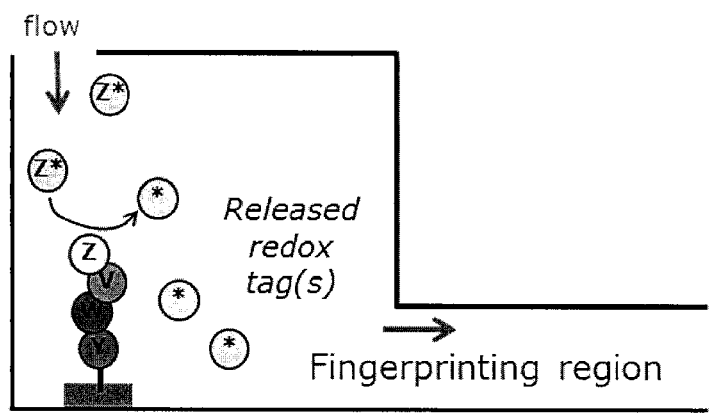
FIGS. 3a-3b are schematics depicting redox fingerprinting detection in accordance with various embodiments of the present teachings.
Figure 3B:
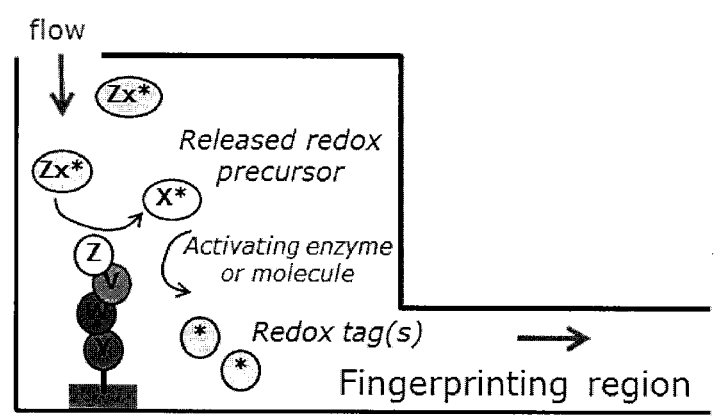

FIGS. 3a-3b are schematics depicting redox fingerprinting detection in accordance with various embodiments of the present teachings. As shown in FIG. 3a, following an on-site reaction, redox tags can be released directly from reactant molecules of the biopolymer and then detected in the fingerprinting region. In embodiments, as shown in FIG. 3b, redox tags can be released indirectly. For example, an on-site reaction may first produce a redox precursor. The redox precursor can then be activated by using activating enzymes or other molecules to produce active redox tags. The produced redox tags can be subsequently detected in a physically separated fingerprinting region, with molecular movement induced by fluid flow.

Figure 3C:
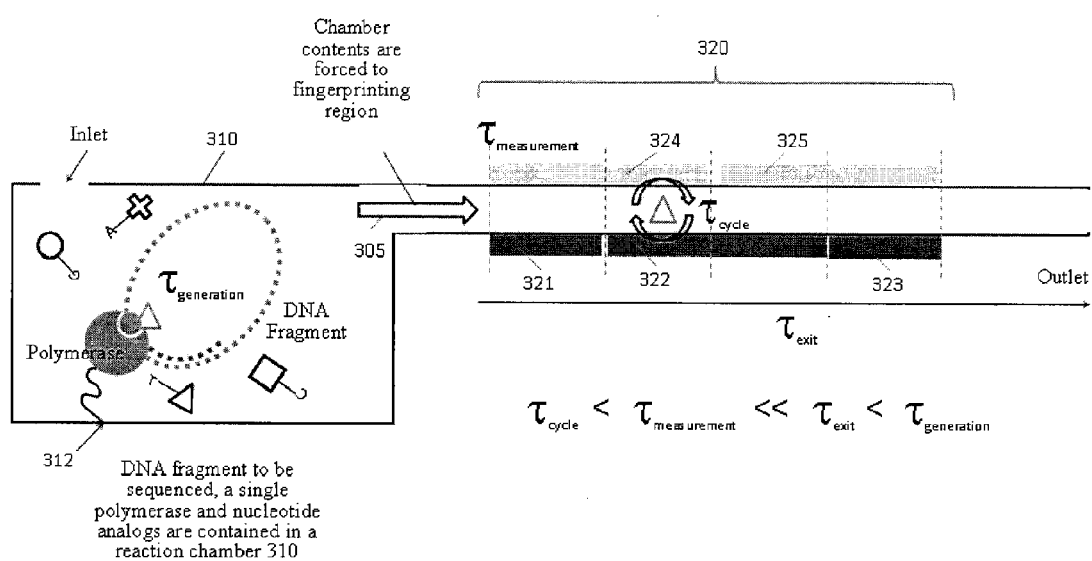
FIG. 3c depicts an exemplary method of DNA sequencing in accordance with various embodiments of the present teachings.

In FIG. 3c, a single polymerase is selectively immobilized in a reaction chamber 310 with the DNA fragment to be sequenced engaged to the polymerase. The reaction chamber 310 can be kept filled with a supply of redox-tagged nucleotides which are not redox active before incorporation. The incorporation of complementary nucleotides may run in real-time. Redox (inactive) tag with extra phosphate group may be released upon incorporation. That is, after incorporation, released tag is converted to a redox active tag by cleaving the phosphate group to take the remaining phosphate group off the molecule.

A fingerprinting region 320 can be connected to the reaction chamber 310 and a pressure gradient may ensure unidirectional travel of chamber contents including for example, byproducts from the reactions through the nanogap of the fingerprinting region 320. Each electrode in the fingerprinting region 320 may be maintained at a unique potential and current can be monitored in real-time for each electrode. In this example, the electrodes are separated having a nanogap of about 50 nm so that as the chamber contents or any molecules pass through the nanogap, molecule diffuses due to Brownian motion between the first and the second (e.g., the top and bottom) electrodes. Note that as the molecule passes through, only appropriately biased set of electrodes can allow the redox tag molecule to shuttle electrons between the electrodes, i.e., to perform redox cycling. By monitoring the current at each electrode the tag molecule can be identified (fingerprinted). By monitoring the electrode current as a function of time the sequence of the DNA can be determined and assembled.

The DNA sequencing process may be controlled. For example, by controlling reaction conditions, such as nucleotide concentrations, the nucleotide incorporation rate $\tau_{generation}$ can be controlled such that the time length or time window between two nucleotide incorporation events is sufficiently long to allow a single molecule to be detected. In other words, the time window determined by $\tau_{generation}$ may allow the nanogap in the fingerprinting region 320 to identify signature of the redox species before the next redox species is generated. In one embodiment, $\tau_{generation}$ may be 1 nucleotide per second. By sequentially measuring the redox signatures of the DNA strand as it is being synthesized in one transducer element, the DNA template sequence can be determined. In embodiments, time lengths that are used to control or engineer the sequencing process to determine sequence information of DNA may include, for example, $\tau_{generation}$ an average time for the incorporation event, $\tau_{exit}$, an average time for a molecule to exit the outlet region, $\tau_{measurement}$, a time scale that the measurement electronics (e.g., by the IC chip including the readout circuitry) can measure current, and $\tau_{cycle}$, an average time for a molecule to shuttle between electrodes, where $\tau_{cycle} < \tau_{measurement} \leq \tau_{exit} < \tau_{generation}$.

During the sequencing process, in order to increase the possibility of detecting each released redox species and to prevent stochastic behavior of the single molecule redox tag (so the molecule does not drift out of the transducer area), an active drift mechanism is incorporated in the transducer element to direct flow of the chamber content including release redox species. For example, a pressure gradient can be generated between the inlets and outlets of the transducer elements by a hydrodynamic mechanism. Alternatively a heating element (see FIG. 12) can be used to create a local temperature gradient so that the redox species flow is unidirectional through the nanogap in the fingerprinting region.

Figure 4:
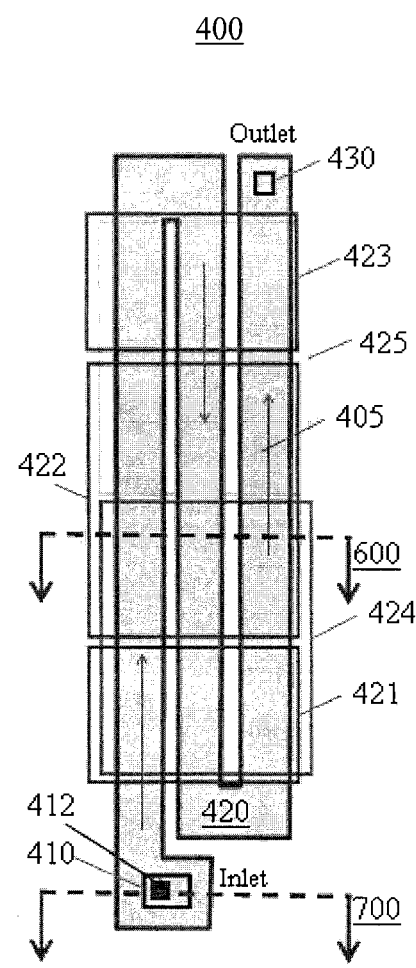
FIG. 4 depicts an exemplary transducer element in accordance with various embodiments of the present teachings.

FIG. 4 depicts a top view schematic of an exemplary transducer element 400 including an inlet region having a reaction chamber 410, a fingerprinting region 420, and an outlet region 430. The reaction chamber 410 can have a material specific attachment site 412, e.g., for single enzyme immobilization. In one embodiment, the transducer element 400 can be made, e.g., about 20×5 µm$^2$. The exemplary transducer element 400 can include, e.g., at least one, such as at least four electrodes configured (e.g., see 421, 422, 423, 424, and 425) along with the nanogap for the byproducts or any chamber contents from the reaction chamber 410 to run through the fingerprinting region 420 along a direction 405. The flow in the nanogap can be initiated and controlled by a pressure and/or temperature gradient between the inlet and the outlet regions of the transducer elements. The nanogap in the fingerprinting region can have desired length and configurations along direction 405. During DNA sequencing, one or more or all of the electrodes of the at least four electrode sets in one transducer element may be electrically biased and monitored by the coupled IC system to identify corresponding redox-tagged nucleotides and thus the sequence information for the DNA fragment to be sequenced.

Figure 5:
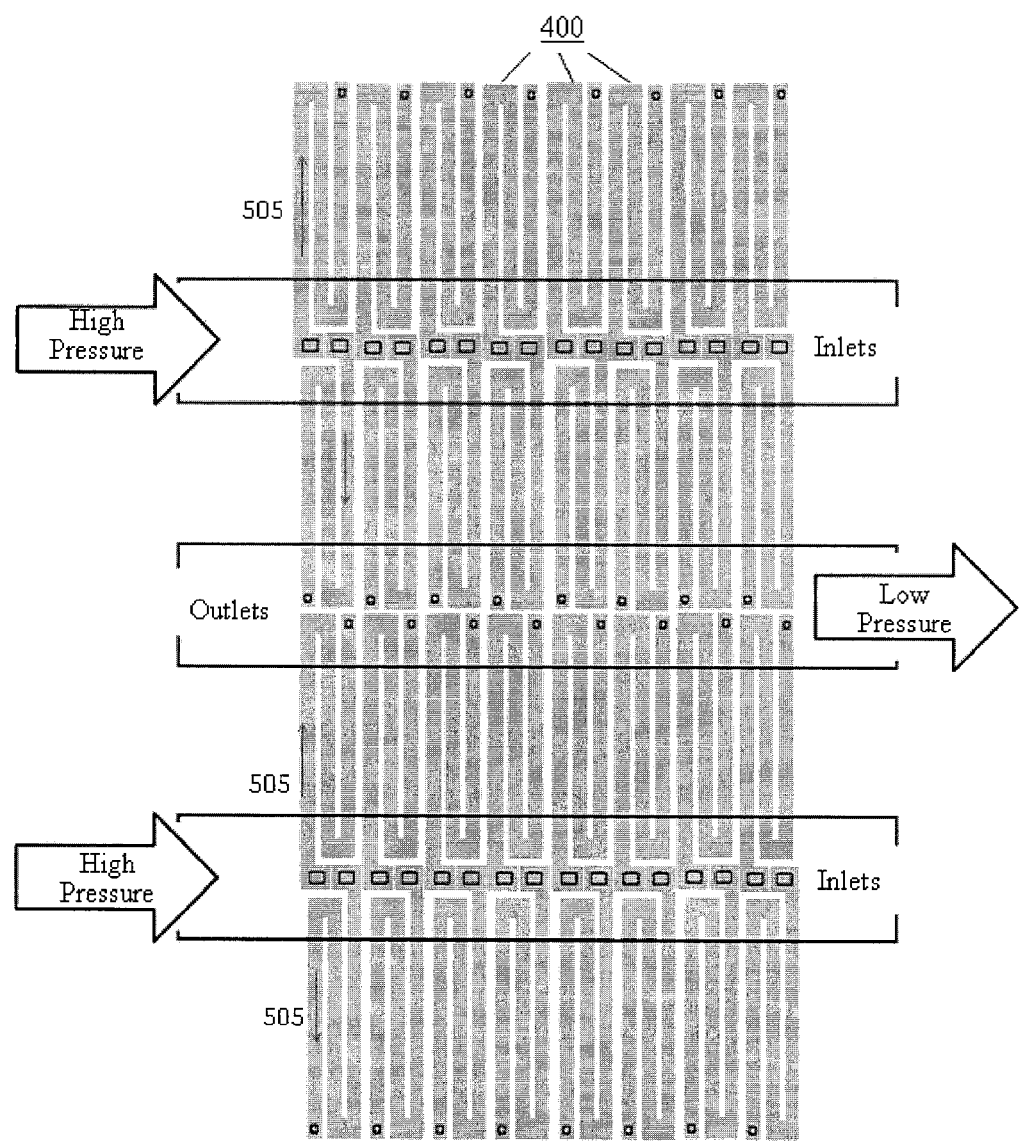
FIG. 5 depicts an exemplary transducer array in accordance with various embodiments of the present teachings.

FIG. 5 depicts an exemplary array including a plurality of transducer elements 400 in accordance with various embodiments of the present teachings. Note that although FIG. 5 shows 8×4 transducer elements in the arrayed format, one of ordinary skill in the art would appreciate that more or less transducer elements may be configured in an arrayed format and any kinds of array can be encompassed within the scope of the present teachings. For example FIG. 5 depicts an array of rectangle, however other array formats may be included without limitation. In one embodiment, inlets of a certain number of transducer elements can be aligned at a high pressure end for applying high pressure to provide a pressure gradient along with the nanogaps of related transducer elements, while outlets of a certain number of transducer elements can be aligned at a low pressure end of the pressure gradient such that fluid in the nanogaps can flow in a controllable direction, e.g., see direction 505. In embodiments, at inlet regions, additional fluidic channels can be configured or aligned to supply, e.g., redox-tagged nucleotides (or nucleotide analogs) and to provide high pressure to maintain a unidirectional flow through the fingerprinting region containing a nanogap between electrodes. Likewise, at outlet regions, additional fluidic channels may be configured and aligned to keep the lower pressure to ensure the unidirectional flow to the outlet regions. In embodiments, desired number of transducer elements (or arrays) may be configured and/or arrayed, for example, to form an array of 1000×1000 transducer elements (or arrays) having a total area of 1 cm$^2$. In embodiments, a PDMS or plastic piece with channels aligned on the inlet regions and outlet regions of the transducer elements may allow for creation of pressure gradient between the inlets and outlets of the transducer elements in a scalable fashion. With the given dimensions and assuming an effective 1 kb fragment on each transducer, 1 billion bases can be sequenced on a 1 cm$^2$ area in less than one hour, if on the order of 1 base/second.

Figure 6:
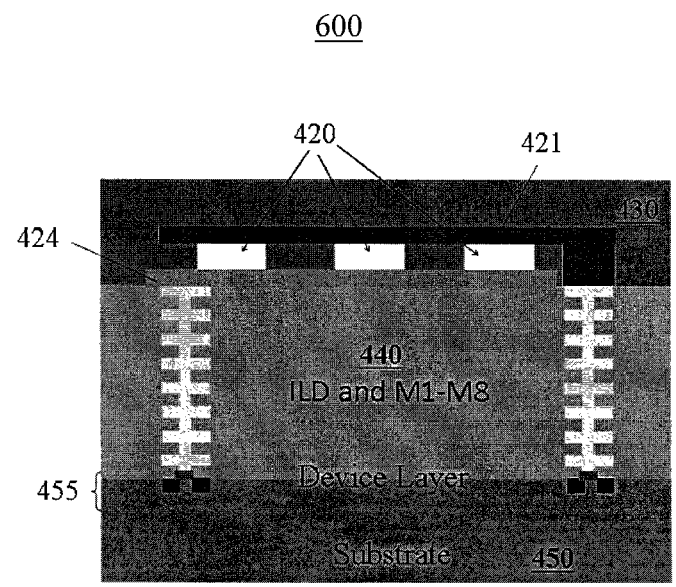
FIG. 6 depicts a cross-section of a fingerprinting region of an exemplary transducer element in accordance with various embodiments of the present teachings.
Figure 7:
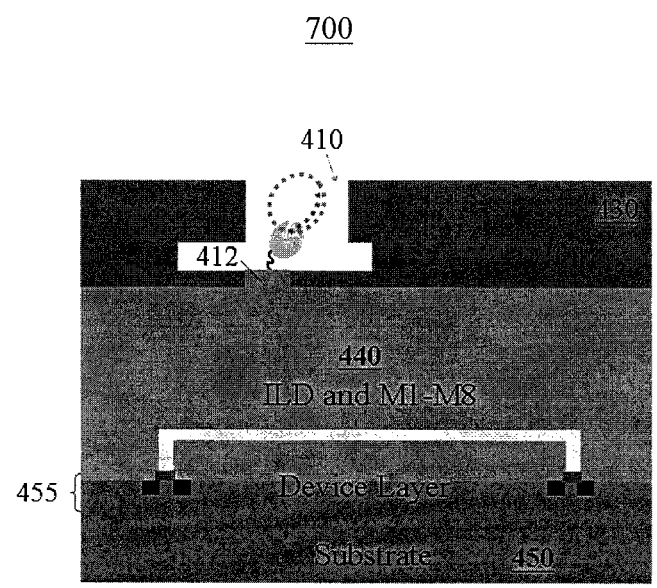
FIG. 7 depicts a cross-section of an inlet region having a reaction chamber of an exemplary transducer element in accordance with various embodiments of the present teachings.

As disclosed herein, the transducer elements for detecting the redox signals can be integrated or coupled on surface of an integrated circuitry IC which may include a readout circuitry for reading and interpreting the redox signal from the single molecule transducer array. FIG. 6 depicts cross section view 600 of a fingerprinting region of one exemplary transducer element in FIGS. 4-5 in accordance with various embodiments of the present teachings. FIG. 7 depicts cross section view 700 of an inlet region of one exemplary transducer element in FIGS. 4-5 in accordance with various embodiments of the present teachings.

As depicted in FIGS. 6-7, the array of transducer elements in FIGS. 4-5 can be disposed on an IC chip formed on a substrate 450. In this example, the IC chip may include a device layer 455 and/or an ILD (i.e., inter level dielectric) layer 440.

The transducer element, at least including the fingerprinting region with nanogaps 420 of FIG. 6 and the reaction chamber 410 of FIG. 7, may be reliably fabricated in a CMOS compatible manner allowing dense integration of transducer elements onto a single platform. For example, transducer array for single molecule fingerprinting may be tightly coupled with readout circuitry, e.g., directly on top of standard CMOS circuits by monolithic integration. The transducer elements and their arrays may be fabricated through post processing a CMOS fabricated device wafer in order to monolithically integrate the transducer elements with signal processing circuitry.

The nanogap 420 may include a first electrode 421 and a second electrode 424. Electrode materials can be made from Pt, Gold, Diamond or other electrochemically active and feasible materials. Fluid channels or the nanogaps can be formed by etching a sacrificial material as known to one of ordinary skill in the art. Depending on the transducer array density and the technology at the time of manufacturing, through silicon vias (TSV), for example, can be used to fabricate the CMOS electronics and transducer portions on separate wafers, followed by integration of components on separate dies. It is also possible to integrate sensor and CMOS components with other packaging technologies.

The transducer elements or their arrays may be integrated with a readout system, e.g., an on-chip readout circuit, which may be designed to have desired sensitivity to realize the transducer density. Such readout system may be formed within the IC chip, e.g., as shown in FIGS. 6-7, disposed between the substrate 450 and the fingerprinting region including electrodes 421 and 424, and nanogaps 420.

The on-chip readout circuitry can be designed to have the necessary sensitivity and foot print to realize the transducer density as needed. Multiple transducer elements may (or may not) share the same readout circuitry in one single platform. The readout circuitry may be coupled with the first and the second electrodes of a nanogap to read and interpret signals from the redox cycling reaction. In embodiments, various circuit schemes may be used, including, e.g., subtraction of top and bottom electrode currents (e.g., see FIG. 8) before readout, implementing transimpedance amplifiers to amplify the signal and using cross-correlation signal processing techniques (on-chip or in off-chip data analysis) to reduce the amplifier noise (e.g., see FIG. 9), and using these scheme in a time domain multiplexed fashion to allow for sharing of the readout circuitry among multiple electrode pairs (e.g., see FIG. 10).

Figure 8:
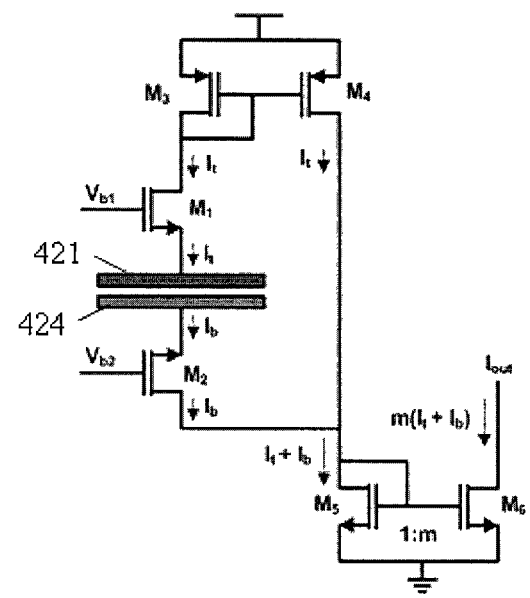
FIGS. 8-11 depict various exemplary readout circuits in accordance with various embodiments of the present teachings.

FIG. 8 is an example of readout circuit to implement subtraction of currents of a first (e.g. top) electrode 421 and a second (e.g., bottom) electrode 424. This operation may reinforce the anticorrelated redox signal. The scheme uses two common gate amplifiers (M1 and M2) which set the electrode potentials approximately Vb1-Vt and Vb2-Vt (Vt is the threshold voltage) while relaying the electrode current to either a current mirror formed by M3/M4 (which inverts it) or to the summing node directly. The current mirror formed by M5 and M6 provides amplification and an interface to a current-mode ADC or other means of acquiring the resulting current which can be shared between many electrode pairs.

Figure 9:
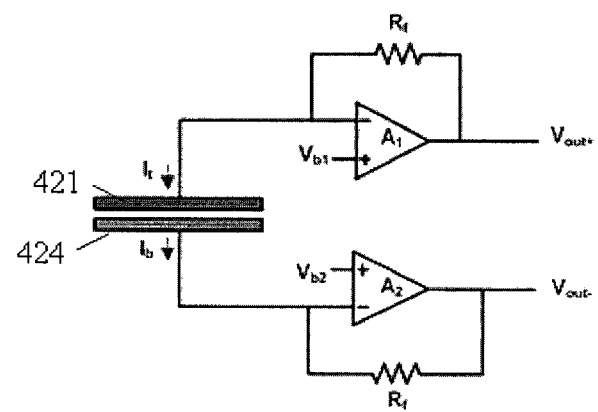

FIG. 9 is an example of readout circuit for a transducer element containing a nanogap having a first (e.g. top) electrode 421 and a second (e.g., bottom) electrode 424. In this embodiment, both electrode signals are acquired independently so that cross-correlation signal processing techniques can be used to reduce the impact of the amplifier (A1 and A2) noises. While drawn here as operational amplifiers with resistive feedback, the transimpedance amplifier (TIA) can be implemented in many different ways. The transducer biasing is controlled by the positive input of the TIA.

Figure 10:
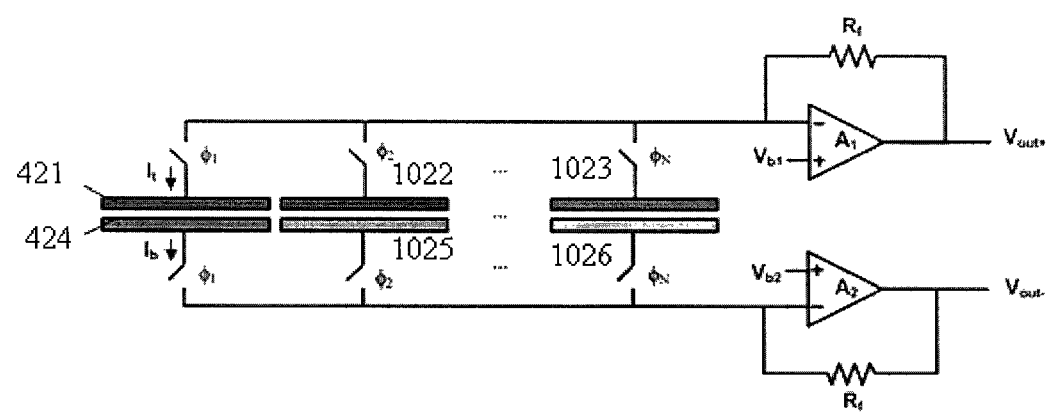
Figure 11:
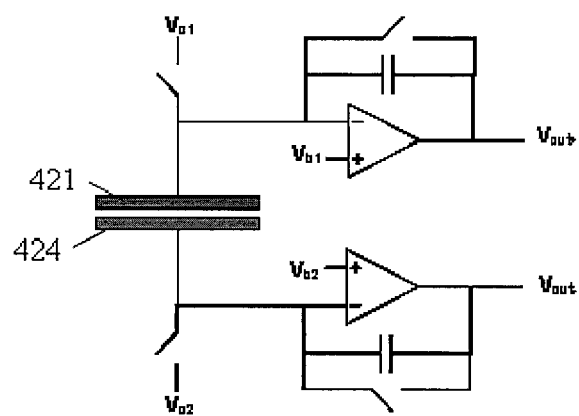

FIG. 10 is an extension of the readout circuit in FIG. 9, where the TIA is shared among many electrodes, see 421, 424. 1022, 1025, 1023, and/or 1026. Switches controlled by non-overlapping control signals are selected between the different nanogap electrodes. The signal of the electrodes is again acquired independently to facilitate cross correlation signal analysis. This scheme is used in a time domain multiplexed fashion to allow for sharing of the readout circuitry among multiple electrode pairs FIG. 11 is a switched capacitor implementation of a pair of TIAs with two separate outputs, which can be used for cross-correlation or similar signal processing. Furthermore, the other switches (e.g., see $V_{o1}$, $V_{o2}$) can implement controllable current cancellation (switches can either be connected to a voltage source or to a capacitor). By means of logic controlling the switches, it is possible to implement hardware subtraction or detection of anti-correlated currents at the electrodes. As shown in FIG. 11, a switched capacitor approach can be used to implement the transimpedance amplifier as well as perform background subtraction of the current traces (to ideally remove any portion not due to the single-molecule redox tags) as well as implementing some level of cross-correlation in the circuitry.

In embodiments, various other possible devices/systems including transducer elements and their arrays, and methods thereof may be encompassed in accordance with various embodiments of the present teachings. For example, FIG. 12 depicts an alternative transducer element in which a heating element (e.g., a nanowire heater) is used to create a heat gradient through the fingerprinting regions to unidirectionally drive the flow of the reaction by-products or any chamber content.

Figure 12:
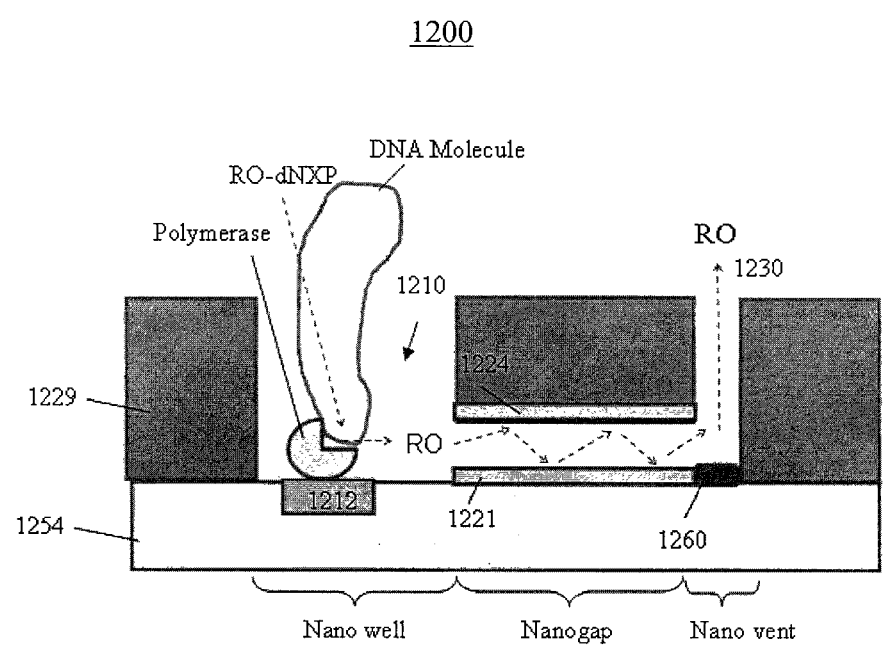
FIG. 12 depicts another exemplary transducer element in accordance with various embodiments of the present teachings.

As shown in FIG. 12, an device 1200 may include an transducer element having a reaction chamber 1210 connected to a fingerprinting region, which may be formed in a dielectric layer 1229, e.g., a post processed layer formed on a CMOS-based semiconductor substrate 1254. The transducer element disposed or fabricated on the substrate surface may include a first (bottom) electrode 1221 and a second (upper) electrode 1224 wherein the first and the second electrodes are each coupled to conducting lines (not illustrated) through which voltage can be applied to the first and second electrodes independently and a current can be measured from each of the first and second electrodes independently. The first electrode 1221 has a face and the second electrode 1224 has a face and the face of the first electrode is separated from the face of the second electrode by a distance or a nanogap that is less than 500 nm. The reaction chamber 1210 is capable of containing a fluid and/or for chemical reactions. The reaction chamber 1210 has a material specific attachment site. For example, the reaction chamber 1210 may have a surface with material specific attachment site 1212 for immobilizing enzymes such as single molecule polymerase for reaction and incorporation of nucleoacids. Fluid or chamber content in the reaction chamber 1210 may be able to flow through the nanogap between the first and second electrodes 1221 and 1224. The layer 1229 of dielectric material may be disposed on the second electrode 1224 and provide an access hole to the reaction chamber 1210. The transducer element may include a heating element 1260 such as a nanowire heater configured at the outlet end 1230 of the fingerprinting regions to create a heat gradient through the fingerprinting regions to unidirectionally drive the flow of the reaction byproducts from the reaction chamber 1210. In an exemplary embodiment, the device 1200 may include a nanowell reaction chamber at an inlet region, a fingerprinting region containing nanogap having electrodes for redox cycling, a nanowire heater, and/or a nano vent at an outlet region, as illustrated in FIG. 12.

In this manner, single DNA polymerase for DNA sequencing can be combined with nanogap detection for single molecule fingerprinting to enable schemes of electrical detection. In one example, multiple redox detections, sequentially or simultaneously performed in a single transducer element and/or sequentially or simultaneously performed in multiple transducer elements, can enable real-time and homogeneous reaction for electrical detection, which provide a portable, accurate, cost effective, and easy-to-use device/sensing system/method for high throughput DNA sequencing.

While the invention is described and illustrated here in the context of a limited number of embodiments, the invention may be embodied in many forms without departing from the spirit of the essential characteristics of the invention. The illustrated and described embodiments, including what is described in the abstract of the disclosure, are therefore to be considered in all respects as illustrative and not restrictive. The scope of the invention is indicated by the appended claims rather than by the foregoing description, and all changes that come within the meaning and range of equivalency of the claims are intended to be embraced therein.

What is claimed is:

1. A method comprising:
   obtaining a transducer array comprising a plurality of transducer elements, each transducer element comprising at least a reaction chamber and a fingerprinting region, wherein the fingerprinting region comprises at least one electrode set comprising a first electrode separated from a second electrode by a nanogap to enable a redox cycling reaction;
   providing a latent redox tagged probe molecule, a catalyst, and a target molecule in the reaction chamber of at least one transducer element; and
   flowing a chamber content from the reaction chamber and through the fingerprinting region to detect the redox cycling reaction in the nanogap between the first and the second electrodes that are biased to identify a corresponding redox-tag;
   wherein the providing a latent redox tagged probe molecule, a catalyst, and a target molecule in the reaction chamber comprises providing (a) redox-tagged amino acids, a protease, and a peptide linker site in the reaction chamber or (b) an enzyme probe with latent redox tag, and a peptide target in the reaction chamber.

2. The method of claim 1, wherein the corresponding redox-tag is directly or indirectly released from the probe molecule in the chamber content.

3. The method of claim 1, wherein the redox cycling reaction detects an enzyme activity, a cell adhesion, a protein binding, and combinations thereof.

4. The method of claim 1, wherein the transducer array is coupled with a readout circuit to read and interpret a signal from the redox cycling reaction.

5. The method of claim 1, wherein the transducer array is coupled with a readout circuit to individually or in groups address one or more transducer elements of the plurality of transducer elements in the transducer array.

6. The method of claim 1, further comprising changing an electrical bias on the first and the second electrodes to monitor a second redox cycling reaction.

7. The method of claim 1, further comprising applying an electrical bias on the at least one electrode set of each of the one or more transducer elements of the plurality of transducer elements in the transducer array to detect a redox cycling reaction in parallel in the one or more transducer elements.

8. The method of claim 1, wherein flowing the chamber content comprises using an active drift mechanism to unidirectionally direct the flow of the chamber contents.

9. The method of claim 1, wherein $\tau_{cycle} < \tau_{measurement} \leq \tau_{exit} < \tau_{generation}$, and wherein $\tau_{generation}$ is an average time for an incorporation event, $\tau_{exit}$ is an average time for a molecule in the reaction chamber to exit the fingerprinting region, $\tau_{measurement}$ is a time scale for electronically measuring current of the first and second electrodes, and $\tau_{cycle}$ is an average time for the redox cycling between electrodes.

10. The method of claim 1, further comprising simultaneously or sequentially flowing the chamber content from one or more reaction chambers of the transducer array.

11. The method of claim 1, further comprising:
flowing the chamber content from the reaction chamber and through the fingerprinting region to detect the redox cycling reaction in the nanogap between the first and the second electrodes that are appropriately biased to identify a corresponding redox-tag.

12. The method of claim 1, wherein the fingerprinting region comprises at least four electrode sets further comprising:
electrically biasing one or more of the at least four electrode sets in at least one transducer element;
wherein the transducer array is coupled with a readout circuit for implementing subtraction of the first and second electrode currents to reinforce anticorrelated redox signal, independently acquiring first and second electrode signals to reduce impact of amplifier noises by cross-correlation signal processing, using a switched capacitor implementation of a pair of transimpedance amplifiers with two separate outputs, or a combination thereof.

13. The method of claim 12, wherein providing a latent redox tagged probe molecule, a catalyst, and a target molecule in the reaction chamber comprises providing a single polymerase, a DNA fragment to be sequenced, and redox-tagged nucleotides in the reaction chamber.

14. The method of claim 13, further comprising determining sequence information for the DNA fragment to be sequenced based on the identified redox-tagged nucleotides.

15. The method of claim 13, further comprising monitoring a signal from the redox cycling reaction as a function of time to determine a sequence of the DNA fragment to be sequenced.

16. The method of claim 13, further comprising detecting or reading a DNA fragment of about 1-100 kilo bases long.

17. The method of claim 13, wherein providing a single polymerase, a DNA fragment to be sequenced, and redox-tagged nucleotides in the reaction chamber comprises immobilizing the single polymerase on surface of the reaction chamber, the reaction chamber comprising the DNA fragment to be sequenced; and supplying the redox-tagged nucleotides to the reaction chamber.

18. The method of claim 12, wherein the transducer array is coupled with a readout circuit to read and interpret a signal from the redox cycling reaction.

19. The method of claim 12, wherein the redox cycling reaction is in situ detected in real-time in the fingerprinting region, upon a complimentary base incorporation in the reaction chamber.

20. The method of claim 12, further comprising changing an electrical bias on each electrode set to monitor a corresponding redox cycling reaction.

21. The method of claim 12, further comprising detecting the redox cycling reaction in parallel in each of one or more transducer elements selected from the plurality of transducer elements.

22. The method of claim 12, wherein flowing the chamber content comprises using an active drift mechanism to unidirectionally direct the flow of the chamber contents.

23. The method of claim 12, wherein $\tau_{cycle} < \tau_{measurement} \leq \tau_{exit} < \tau_{generation}$, and wherein $\tau_{generation}$ is an average time for an incorporation event, $\tau_{exit}$ is an average time for a molecule in the reaction chamber to exit the fingerprinting region, $\tau_{measurement}$ is a time scale for electronically measuring current of the first and second electrodes, and $\tau_{cycle}$ is an average time for the redox cycling between electrodes.

24. The method of claim 12, wherein the redox-tagged nucleotides comprise at least four redox-tagged nucleotides with four redox tags respectively labeling four different nucleotides.

25. The method of claim 12, further comprising conducting a whole genome sequencing by combining information from each transducer element of an array comprising a number of transducer elements to generate a complete order and identity of every base in the genome.

26. The method of claim 12, further comprising simultaneously or sequentially flowing the chamber content from one or more reaction chambers of the transducer array.

27. The method of claim 12, further comprising:
flowing the chamber content from the reaction chamber and through the fingerprinting region to detect the redox cycling reaction in each nanogap of the electrically biased one or more electrode sets to identify corresponding redox-tagged nucleotides.

* * * * *